(12) United States Patent
Jong et al.

(10) Patent No.: US 7,241,891 B2
(45) Date of Patent: Jul. 10, 2007

(54) METHOD FOR THE PURIFICATION OF PIRIBEDIL

(75) Inventors: Shean-Jeng Jong, Tao-Yuan (TW); Yu-Sheng Lin, Tao-Yuan (TW)

(73) Assignee: Chung-Shan Institute of Science & Technology, Lung-Tan, Tao-Yuan (TW)

( * ) Notice: Subject to any disclaimer, the term of this patent is extended or adjusted under 35 U.S.C. 154(b) by 451 days.

(21) Appl. No.: 10/810,799

(22) Filed: Mar. 29, 2004

(65) Prior Publication Data

US 2005/0215788 A1 Sep. 29, 2005

(51) Int. Cl.
*C07D 403/04* (2006.01)
(52) U.S. Cl. ...................................... 544/295
(58) Field of Classification Search ................. 544/295
See application file for complete search history.

(56) References Cited

U.S. PATENT DOCUMENTS 3,299,067 A * 1/1967 Laubie et al. ............... 544/295

FOREIGN PATENT DOCUMENTS

PL 167397 * 8/1995

OTHER PUBLICATIONS

English Translation of the document PL 167397 published Aug. 1995.*

* cited by examiner

*Primary Examiner*—Deepak Rao
(74) *Attorney, Agent, or Firm*—Bacon & Thomas PLLC

(57) ABSTRACT

A method for purifying Piribedil includes mixing Piribedil solid having a purity of 98% by weight with water, boiling the mixture, adding slowly 95% ethanol to the boiling mixture to form a clear liquid, filtering the hot clear liquid, cooling the filtrate to obtain a white crystal having a purity of 99.8% by weight of Piribedil.

10 Claims, No Drawings

METHOD FOR THE PURIFICATION OF PIRIBEDIL

FIELD OF THE INVENTION

The present invention is related to a method for purifying 2-[1'(3",4"-methylenedioxy benzyl)-4-piperazinyl]-pyrimidine, which is also known as Piribedil, and in particular to a method for purifying Piribedil from a purity of 98 wt % or lower to 99.8 wt %.

BACKGROUND OF THE INVENTION

Piribedil is 2-[1'(3",4"-methylenedioxy benzyl)-4-piperazinyl]-pyrimidine, and its chemical structure is as follows:

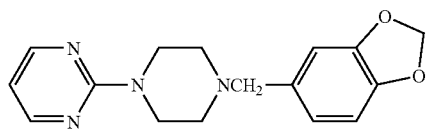

According to the disclosures in U.S. Pat. Nos. 3,299,067 (1967) and 5,362,731 (1994), and Polish patent No. PL 167397 (1995), Piribedil is useful in treating a patient suffering Parkinson's disease or hyperactive bladder, and it can also be used as a peripheral vasodilator, analgesic agent or anti-inflammatory agent.

Polish patent No. PL 167397 (1995) discloses a method of the synthesis of Piribedil comprising reacting 1-(2-pyrimidinyl)piperazine and piperonal in the presence of a reducing agent, formic acid, at a temperature of 100–140° C. The reaction can be represented by the following equation:

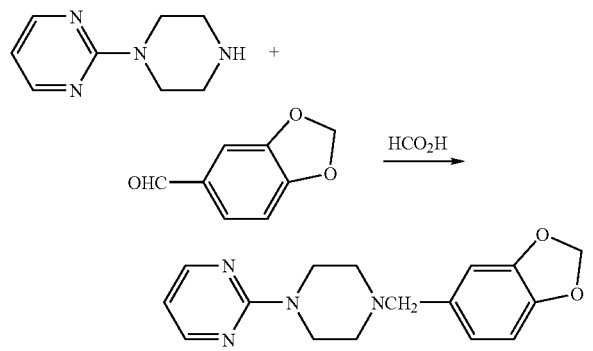

This synthesis method is recognized as the simplest method for the preparation of Piribedil. However, the Piribedil product prepared by this method is a light yellow powder having a purity of 98 wt %.

The inventors of the present application have made an approach to purify this Piribedil product including adding this Piribedil product into anhydrous ethanol or 95 wt % ethanol, boiling the resulting mixture, and re-crystallizing. The re-crystallized Piribedil product becomes darker in color and lower in purity. Another approach made is similar to the first approach but further includes a de-coloring step with activated carbon before the re-crystallization. However, the Piribedil purity is not enhanced.

Therefore, there is a need in the industry for a method of the purification of Piribedil, which can increase the purity of the Piribedil product from 98 wt % to a higher purity.

SUMMARY OF THE INVENTION

The present invention provides a method for purifying Piribedil comprising the following steps: a) mixing a Piribedil product having a Piribedil purity of 98 wt % or lower with water; b) heating the resulting mixture to boiling or a temperature near boiling; c) adding ethanol to the hot mixture from step b) while maintaining a temperature of the resulting mixture at 60–100° C., so that a clear liquid is obtained; d) filtering the hot clear liquid; e) cooling the resulting filtrate to form a crystal therein; and f) removing the crystal from the filtrate and drying the crystal to obtain a white solid having a Piribedil purity higher than 98 wt %.

Preferably, the Piribedil product having a Piribedil purity of 98 wt % or lower used in step a) has a Piribedil purity of 98 wt %.

Preferably, in step a) the Piribedil product having a Piribedil purity of 98 wt % or lower is mixed with water in a ratio of per kilogram of the Piribedil product 0.1–10 liters of water, and more preferably about one liter of water.

Preferably, the Piribedil product having a Piribedil purity of 98 wt % or lower is prepared from a method comprising reacting 1-(2-pyrimidinyl)piperazine and piperonal in the presence of formic acid as a reducing agent at a temperature of 100–140° C.

Preferably, the ethanol used in step c) is an aqueous solution having an ethanol concentration of 25–100 wt %, and more preferably 95 wt % ethanol aqueous solution.

Preferably, in step c) the ethanol added is in an amount of 1–100 liters, and more preferably 10 liters, per kilogram of the Piribedil product.

Preferably, the white solid obtained in step f) has a Piribedil purity of 99.8 wt %.

DETAILED DESCRIPTION OF THE PREFERRED EMBODIMENT

The Piribedil purification method disclosed in the invention of the present application will be better understood by the following example, which is merely for illustration, not for the limitation of the scope of the present invention.

EXAMPLE 1

To 1 kg powder having a Piribedil purity of 98 wt % in a 15 L flask equipped with a heating pack and mechanical stirrer one liter of distilled water was added. The mixture was heated to 100° C. Five liters of 95 wt % ethanol aqueous solution was slowly added into the flask while stirring, and the temperature of the mixture contained in the flask was dropped to about 60° C. upon completion of the 95 wt % ethanol. The temperature was increased to 75° C. by heating, and another five liters of 95 wt % ethanol aqueous solution was slowly added into the flask while maintaining the temperature at 75° C. by heating, thereby the opaque mixture was turned into a clear liquid. The hot clear liquid was filtered, and the resulting hot filtrate was cooled with an ice bath, so that a crystal was formed therein. The crystal was recovered by filtration and dried in vacuo to obtain 0.92 kilogram of a white crystallized solid having a Piribedil purity of 99.8 wt %. The Piribedil purity of 99.8 wt % was determined by differential scanning calorimetry (DSC) and high performance liquid chromatography (HPLC).

The invention claimed is:

1. A method for purifying Piribedil comprising the following steps: a) mixing a Piribedil product having a Piribedil purity of 98 wt % or lower with water; b) heating the resulting mixture to boiling or a temperature near boiling; c) adding ethanol to the hot mixture from step b) while maintaining a temperature of the resulting mixture at 60–100° C., so that a clear liquid is obtained; d) filtering the hot clear liquid; e) cooling the resulting filtrate to form a crystal therein; and f) removing the crystal from the filtrate and drying the crystal to obtain a white solid having a Piribedil purity higher than 98 wt %.

2. The method according to claim 1, wherein the Piribedil product having a Piribedil purity of 98 wt % or lower used in step a) has a Piribedil purity of about 98 wt %.

3. The method according to claim 1, wherein in step a) the Piribedil product having a Piribedil purity of 98 wt % or lower is mixed with water in a ratio of per kilogram of the Piribedil product 0.1–10 liters of water.

4. The method according to claim 3, wherein in step a) the Piribedil product having a Piribedil purity of 98 wt % or lower is mixed with water in a ratio of per kilogram of the Piribedil product about one liter of water.

5. The method according to claim 2, wherein in step a) the Piribedil product having a Piribedil purity of 98 wt % is prepared from a method comprising reacting 1-(2-pyrimidinyl)piperazine and piperonal in the presence of formic acid as a reducing agent at a temperature of 100–140° C.

6. The method according to claim 1, wherein the ethanol used in step c) is an aqueous solution having an ethanol concentration of 25–95 wt %.

7. The method according to claim 1, wherein the ethanol used in step c) is an aqueous solution having an ethanol concentration of 95 wt %.

8. The method according to claim 7, wherein in step c) the ethanol added is in an amount of 1–100 liters per kilogram of the Piribedil product.

9. The method according to claim 8, wherein in step c) the ethanol added is in an amount of 10 liters per kilogram of the Piribedil product.

10. The method according to claim 1, wherein the white solid obtained in step f) has a Piribedil purity of 99.8 wt %.

* * * * *